United States Patent
Draper

[11] Patent Number: 5,873,843
[45] Date of Patent: Feb. 23, 1999

[54] ASSESSING THE STATE OF UNION IN A BONE FRACTURE

[75] Inventor: Edward Richard Cornell Draper, Bebbenhall, England

[73] Assignee: BTG International Limited, England

[21] Appl. No.: 676,390

[22] PCT Filed: Feb. 15, 1995

[86] PCT No.: PCT/GB95/00313

§ 371 Date: Jul. 23, 1996

§ 102(e) Date: Jul. 23, 1996

[87] PCT Pub. No.: WO95/22282

PCT Pub. Date: Aug. 24, 1995

[30] Foreign Application Priority Data

Feb. 18, 1994 [GB] United Kingdom ................ 9403158

[51] Int. Cl.$^6$ ................................................ A61B 5/103
[52] U.S. Cl. ........................... 600/587; 600/595; 606/54
[58] Field of Search ........................... 128/774, 782; 606/54, 57; 600/587, 595

[56] References Cited

U.S. PATENT DOCUMENTS

| | | | |
|---|---|---|---|
| 4,576,158 | 3/1986 | Boland | 606/54 |
| 5,207,676 | 5/1993 | Canadell et al. | 606/54 |
| 5,275,599 | 1/1994 | Zbikowski et al. | 606/54 |
| 5,437,668 | 8/1995 | Aronson et al. | 606/54 |
| 5,474,087 | 12/1995 | Nashner | 128/782 |

FOREIGN PATENT DOCUMENTS

| | | |
|---|---|---|
| 0 135 394 | 3/1985 | European Pat. Off. . |
| 0 324 279 | 7/1989 | European Pat. Off. . |
| 2 435 938 | 4/1980 | France . |
| 3912080 | 5/1990 | Germany ........................ 128/774 |
| 2255284 | 11/1992 | United Kingdom ............ 606/54 |
| 2258155 | 2/1993 | United Kingdom ............ 606/54 |
| 93/06779 | 4/1993 | WIPO . |

OTHER PUBLICATIONS

J.B. Richardson et al, "Fracture stiffness measurement in the assessment and management of tibial fractures", Clinical Biomechanics, 1992, No. 7, pp. 75–79.

Engineering in Medicine, vol. 16, No. 4, Oct. 1987, London (GB)pp. 229–232,J.L.Cunningham et al. "The Measurement of Stiffness of Fractures treated with Section Test Equipment and Procedures" See pp. 230–231.

Peruchon, E., et al., Evaluation and control of growth activity of epiphyseal plate, Medical & Biological Engineering & Computing, vol. 18, No. 4 (Jul. 1980), pp. 396–400.

*Primary Examiner*—Richard J. Apley
*Assistant Examiner*—Victor K. Hwang
*Attorney, Agent, or Firm*—Pillsbury Madison & Sutro, LLP

[57] ABSTRACT

The method involves having the subject, to whose fractured limb an external fixator has been applied, undergo a specific load test, measuring the load carried by the fixator and the total load carried by the limb during the test, and determining a measure representing a comparison between the two measured loads. The test is preferably a dynamic one, and a suitable apparatus for carrying out the method is described, which includes a forceplate incorporated in a treadmill assembly to stimulate muscle activity in the limb during the test. The method and device provides an early indication as to whether or not bone healing has started, and thus can be used to provide an advance warning in cases of delayed osseous union.

15 Claims, 2 Drawing Sheets

ASSESSING THE STATE OF UNION IN A BONE FRACTURE

This application claims benefit of international application PCT/ GB95 /00313 filed Feb. 15, 1995.

The present invention relates to medical apparatus, and more particularly to a device and method for use in assessing the state of union in a bone fracture.

External fixators have been widely used in surgery especially for treating traumatic lesions of large bones, where, after fracture reduction, the burden on the fractured bones is instead carried by a fixator during the healing period. The general method involves boring pins into the healthy bone tissue on either side of the fracture and applying a rigid support frame spanning the fracture to the protruding ends of the pins. When healing of the bone tissue is judged to be complete the external fixator can be removed.

Being outside the body means that the fixator frame lies at a distance from the bone and the resulting lever arm can lead to considerable loads on the fixator frame and/or on the bone. On the other hand external fixation has the advantage that the main components of the device are external to the body and therefore accessible. Strain gauge transducers can be incorporated into external fixators for monitoring loads and deformations over the fracture, and such biomechanical monitoring enables an assessment of fracture healing to be made, to supplement radiology and manual examination in determining the timing of the removal of the fixator. If the supporting external fixator is removed prematurely, late angulation and refracture are common important complications.

A number of methods of measuring the state of fracture healing have been developed. For example, in Clinical Biomechanics, 1992, No. 7, pages 75–79, 'Fracture stiffness measurement in the assessment and management of tibial fractures', the authors J B Richardson et al describe the results of fracture bending stiffness tests on a group of patients with tibial fractures treated with external fixators. The fracture healing measure proposed in that paper is a value of fracture bending stiffness in the sagittal plane of 15 Nmdeg$^{-1}$ at which removal of the external fixator and functional loading of the fracture can be prescribed. The article also indicates that such a technique of fracture healing monitoring shows no significant increase in stiffness until about eight weeks after fixation.

In Engineering in Medicine, Vol. 16, No. 4, October 1987, London (GB), pages 229–232, 'The measurement of stiffness of fractures treated with external fixation', J L Cunningham et al, further test equipment and procedures are described for measuring the mechanical stiffness of such fractures. The external fixator described in this publication is fitted with a transducer able to measure loads (eg. torsion, bending) in a number of different directions, and some of the results indicated that increased stiffness may be observed as early as five or six weeks after fixation.

A substantial problem in healing of fractures, especially tibial fractures, is delayed osseous union. Treatment of this problem, by techniques such as bone grafting, should be performed as early as possible. However, conventional techniques using clinical and radiographic examination are slow to detect this problem. Biomechanical monitoring methods involving fracture stiffness, such as those referred to above, provide measures to determine when union is effectively complete and treatment can finish, but do not give an indication as to whether or not the process of healing is properly underway, particularly at the earliest stages of healing.

The aim of the present invention is to improve the above situation and to provide a device and method for use in assessing the state of union in bone fractures, particularly for early detection of delayed osseous union.

In a first aspect, the invention provides a device for use in assessing the state of union in a bone fracture in a limb, the device comprising:

a fixator connectable across the fracture by means of a plurality of elements extendable through respective portions of the fractured bone;

means for providing a measure of the load carried by the fixator;

means for providing a measure of the total load passed through the limb during a specific load test; and signal processing means for processing signals representing the fixator load measure and the total limb load measure, wherein means are provided to stimulate or encourage muscle activity in the limb during the test.

In respect of the means to stimulate or encourage muscle activity in the limb, a treadmill assembly may be provided.

The fixator load measuring means may be arranged to provide a measure of the fixator load in a direction substantially parallel to the long axis of the fractured bone, and for this purpose the fixator preferably allows movement only in said long axis direction, the fixator load measuring means comprising a strain gauge to detect such movement.

In an embodiment of the device, the fixator comprises two separate blocks mounted on a linear bearing, between which blocks is mounted a spring unit incorporating the strain gauge.

Additionally or alternatively, means to measure the bending moment in the fixator may be provided.

Preferably, the total limb load measuring means comprises a forceplate, and this forceplate may form part of the treadmill assembly.

In a second aspect, the invention provides a method for use in assessing the state of union in a bone fracture in a limb of a subject, for which fracture a fixator has been applied, the method comprising the steps of:

subjecting the limb to a specific load test involving the application of muscle loading to the limb;

measuring the load carried by the fixator and the total load passed through the limb during the test; and determining a measure representing a comparison between the measured fixator load and the total limb load.

The load test may be a walking test carried out on a treadmill, the total limb load being determined by measuring the vertical ground force exerted by the limb on the treadmill.

When a walking test is used, it is preferable to consider only a selected part of each step for purposes of determining the load comparison measure, and this selected part may be a central portion of the stance phase of each step.

Preferably, the test is carried out at successive intervals after fixation and the results of successive tests are compared with prescribed results for a fracture of the type in question. In this way, monitoring the progress of the results of the test over time will provide an early indication as to how the fracture healing is progressing.

The comparison measure is preferably a fracture stiffness index (FSI), or its reciprocal, defined as:

$$FSI = \text{Total limb load/Fixator load.}$$

The invention has arisen from the inventor's experimental investigations into the loads carried by a fixator during healing. By way of example, reference is made to the accompanying drawings which illustrate the method and results of the experimental investigations, in which.

Figure 1:
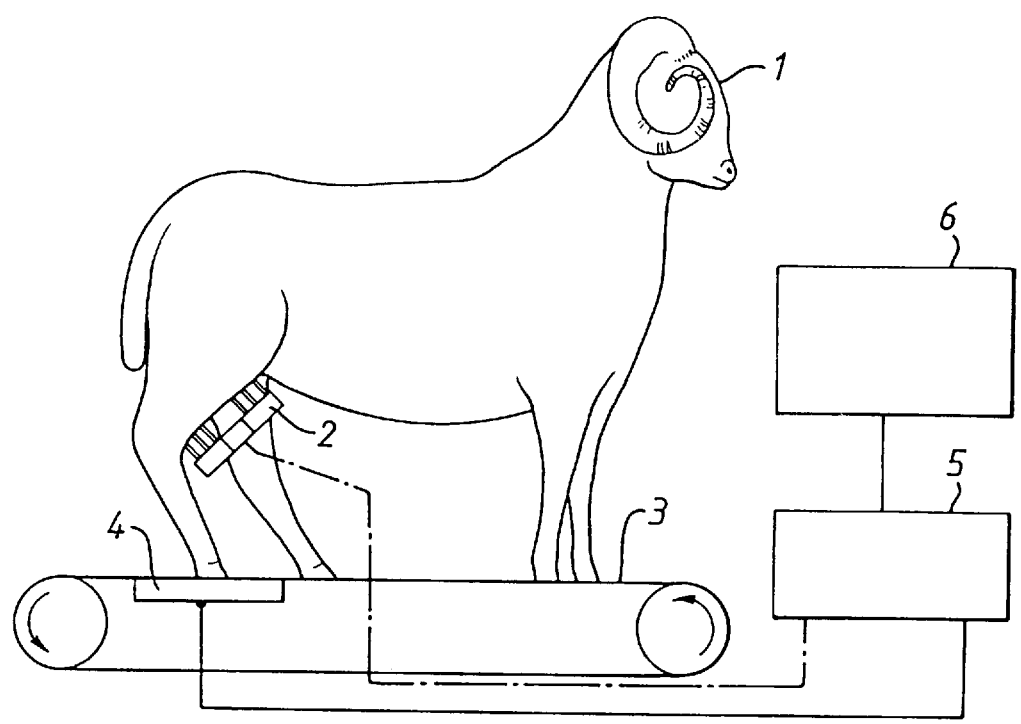
FIG. 1 shows the experimental set-up used.

Experimental Method (FIG. 1)

Two similar groups of blackface ewes had midshaft tibial osteotomies performed. The sheep of one group, referred to henceforth as 'the control group', were then externally fixed with external fixators 2 as described in more detail below, whilst in the case of each of the animals of the other group (referred to here as 'the delayed-union group'), the same device was fixed after the tibia had been stripped of 20 mm periosteum on either side of the osteotomy and then covered by a silicone rubber sheath. In this way, the sheep of this group provided a model of delayed osseous union, as the bone sheathing had the effect of preventing the blood supply from the surrounding muscles from reaching the bone (devascularisation), and thereby delaying union of the fractured tibia.

At weekly intervals thereafter a fracture stiffness index (FSI) was determined for each of the sheep in both groups. The FSI is defined as the total load carried by the involved limb (ie. the instantaneous weight of the animal on that limb) divided by the load on the fixator, as measured during a controlled specific test, in this case a walking test. A specially constructed treadmill 3 was used for these tests, as illustrated in FIG. 1, consisting of an endless belt of a standard belting material driven by an AC induction motor with a variable speed controller. A rectangular forceplate 4 incorporating a load transducer was mounted horizontally below the belt at the same height as the rest of the bed in order to allow measurement of the vertical component of the ground reaction force, representing the total load carried by the limb. The forceplate was designed and positioned such that the right rear hoof of an animal would normally land on it during a walking test, and the other hooves would not. A walking test was used because this allows a considerably greater load to be applied to the broken tibia than would otherwise be practicable, due to the muscular activity involved in such a test. A slow walking speed of 1 m/s was chosen for the tests, and the system was designed so that during a test the animal was able to slow down and stop the belt at will.

Although the treadmill used and described above was specifically constructed for these tests, such devices are in themselves known. A treadmill of this general type is disclosed in International Patent Application WO-93/06779, in this case for application to gait characterisation of a subject.

For the fixator load measurement, the axial load on the fixator was monitored during the tests. Each external fixator 2 incorporated an in-built axial load transducer 15 to measure the fixator axial compression (described further below). During a test, the load measured by this transducer and that measured by the transducer incorporated in the treadmill forceplate 4 were simultaneously recorded. The signals were fed from the transducers to strain gauge amplifiers 5 whose outputs were fed to a microcomputer 6 for recording and analysis.

Each sheep 1 was encouraged to walk by someone standing behind it, and when the animal was walking steadily the test began. The signal from the forceplate transducer was sampled at 50 Hz and only recorded when it exceeded a chosen threshold of 10N, which was above the background noise, in order to define a length of time of the stance phase of each step. The recordings lasted between 2 and 5 minutes during which time 20–150 valid steps could be recorded, valid steps being selected according to defined criteria (based on shape and duration) to avoid the use of signals recorded when the animal stopped or other such problems. The signals were automatically stored on disc by the recording microcomputer 6 for later analysis.

The FSI was calculated from the recorded data for each valid step of each animal in each walking test in the following way. Over the middle half of the stance phase of each step (that is, ignoring the first and last quarters) the vertical ground reaction force signal was divided by the fixator axial compression signal. For each animal, the mean FSI over this middle period was then calculated, and the values so obtained from all the valid steps then averaged for each test, giving the values shown graphically in FIG. 4 and discussed below.

Some of the animals were killed at two weeks and the rest at six weeks in order to perform post-mortem torsional tests to measure the state of union of the tibial fractures directly.

The External Fixator

Figure 2:
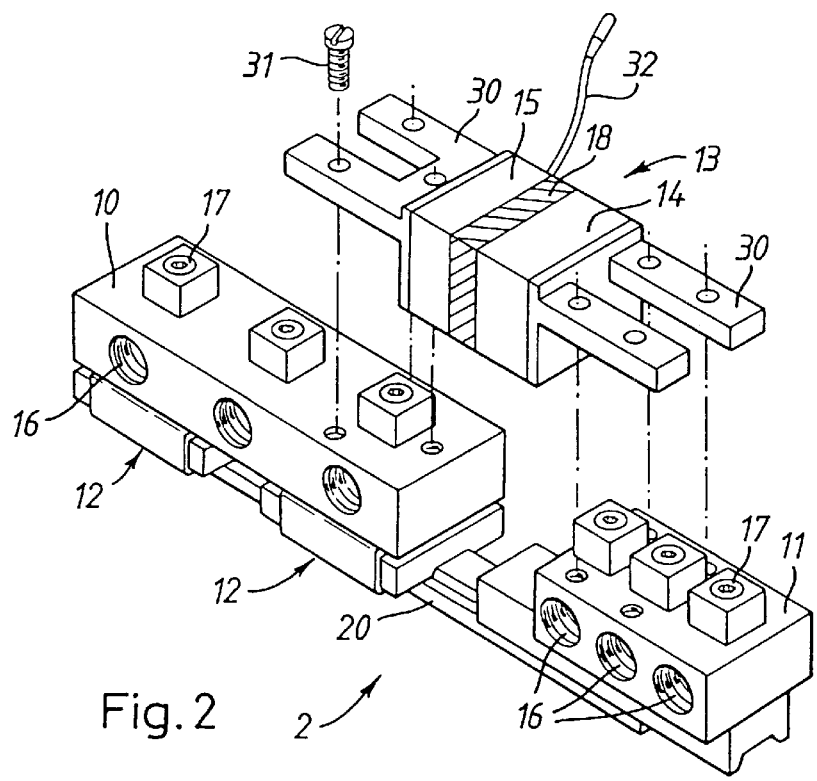
FIG. 2 illustrates in detail the fixator device used in the experiments.

As FIG. 2 shows, the fixator comprises four sections, two separate pin blocks 10 (proximal) and 11 (distal), a linear bearing with two carriages 12, and a module 13 which houses a spring 14 and an axial load transducer 15. The two pin blocks 10 and 11 are each provided with three bores 16 transverse to the longitudinal orientation of the fixator to receive six fixator pins (not shown) which can be firmly clamped in the pin blocks by means of clamping bolts 17.

The proximal pin block 10 is mounted on the two linear bearing carriages 12, while the lower block is bolted directly to a linear bearing track 20, on which the carriages run. This bearing features preloaded re-circulating balls running within two grooves, one on either side of the track, providing the minimum possible play whilst ensuring low friction even under high load. With this device, movement is only possible in the longitudinal direction, which corresponds to the long axis of the bone when the fixator is in position.

The module 13 is mounted between the pin blocks and bolted to them by means of flanged plates 30 and bolts 31, as indicated in FIG. 2. Between the plates 30 the axial load transducer 15 and a spring block 14 are positioned. The spring stiffness of the fixator can be varied if required by replacing one spring block 14 of a known stiffness by another spring block of a different known stiffness. For these experiments, a silicone spring block and an epoxy resin spacer 18 were used, and the stiffness could be altered by varying the relative thicknesses of the two components.

The incorporation of a spring block in the fixator allows a small amount of controlled axial movement which is known to tend to encourage fracture healing. In reduction of the fracture and fitting of the external fixator, a small gap was left between the bone ends across the fracture site. It is to be noted that the experiments described could also have been carried out using rigid fixators incorporating an axial load transducer but allowing effectively no movement between the pin blocks.

A short 125 mm screened lead 32 is connected to the axial load transducer 15. This lead was then connected by a screened cable to a standard strain gauge amplifier for the duration of the tests.

To ensure performance, before each experiment the fixators were stripped down, cleaned and lubricated and the pins and fixator were sterilised. The bearings were additionally periodically lubricated throughout the experiments with a general purpose oil. In attaching the fixator, the fixator pins, which were standard 6 mm diameter Orthofix pins, were screwed into the fractured bone at the desired positions, three on either side of the fracture. The pins were sheathed to a diameter of 10 mm outside the body for extra rigidity. The pins were then introduced into the bores 16 and clamped in place with the clamping bolts 17.

Before each test, the clamping bolts were loosened and the fixator pins then tightened within the bone with a torque wrench. The clamping bolts were then tightened to firmly clamp the pins.

Figure 3:
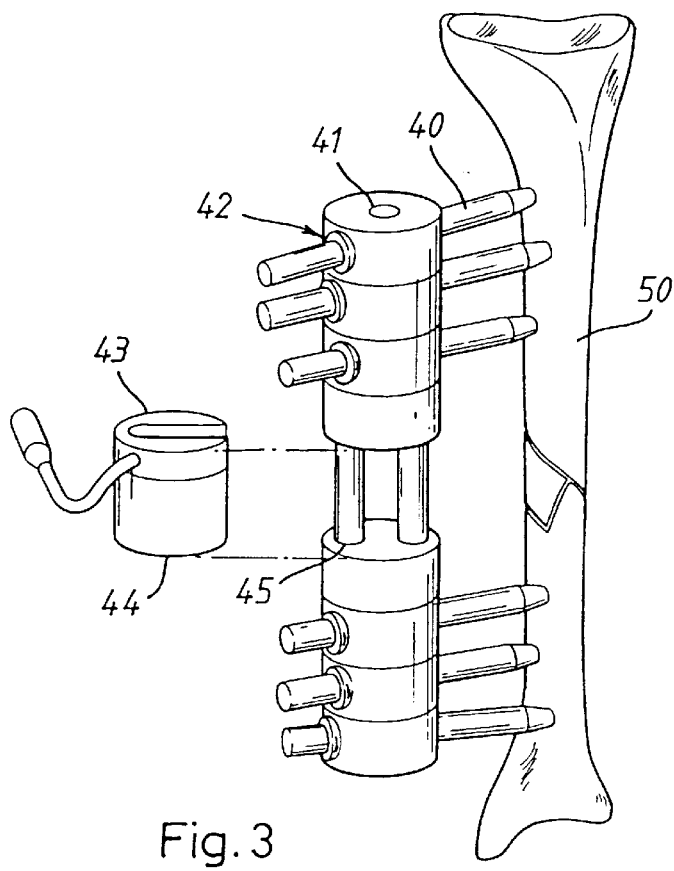
FIG. 3 shows an alternative fixator device.

In the alternative embodiment of a fixator illustrated in FIG. 3, tapered bone pins 40 are shown screwed in place in the fractured bone 50 and clamped in fixator bar 41 by means of pin clamps 42. The module comprising load transducer 43 and spring 44 is shown in detached position, and reference 45 indicates the linear bearings of the device.

Figure 4:
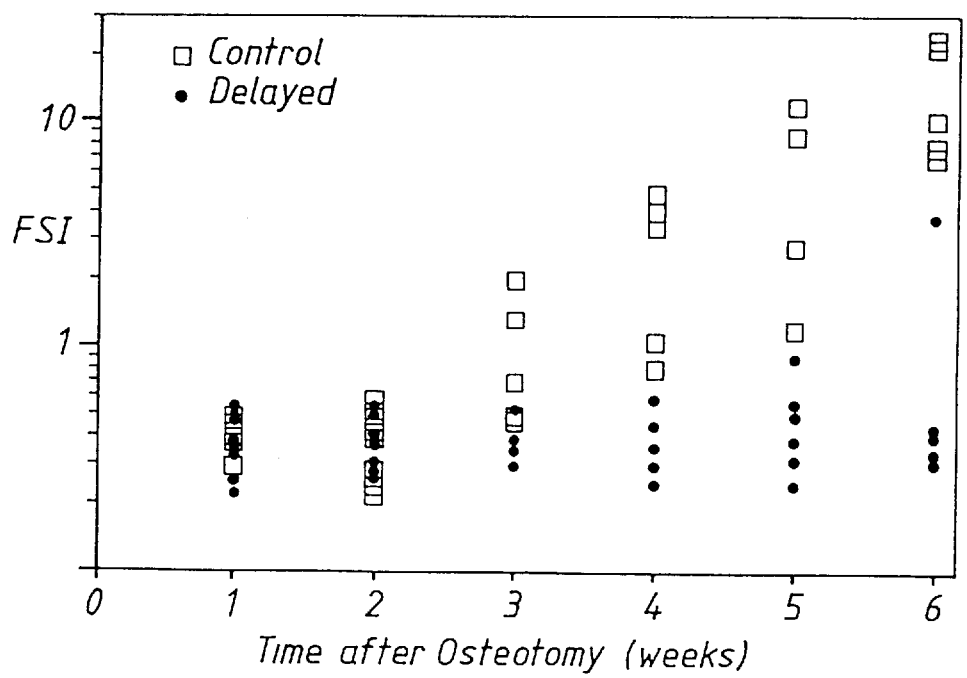
FIG. 4 illustrates the experimental results.

Results (FIG. 4)

In the control group of ewes, a significant increase in FSI was detected after only three weeks from a mean of 0.41 (sd=0.06) at the first week to 0.99 (sd=0.64) at the third week. This was a surprising result, as subsequent radiographs at four weeks showed advancing collars of mineralised callus on either side of the osteotomies, but only very minimal coalescing of these regions, suggesting very little mechanical bridging and hence minimal load bearing capacity across the fracture.

By contrast, in the delayed-union group there was no significant increase in the mean FSI over such a time period, the FSI value going from 0.40 (sd=0.11) at the first week, 0.38 (sd=0.09) at the third week to 0.98 (sd=1.42) at the sixth week. The results are shown graphically in FIG. 4, in which FSI is shown on a logarithmic axis against time after osteotomy in weeks. The graph shows very clearly that by a time only three weeks from surgery in most cases, an indication of the commencement of bone healing can be observed by the level of FSI. At four weeks, there is no overlap at all between the ranges of data for the two groups. In fact, the logarithmic scale of FIG. 4 masks the dramatic rise in FSI values. It can be seen that to begin with, the values for each animal are remarkably similar at around 0.4, until the first detectable stages of healing at which time they rapidly increase, in some cases by an order of magnitude or more.

The post mortem torsional tests performed on the osteotomies confirmed the validity of the delayed union model. For example, of six sheep of the delayed union group killed at two weeks all six tibiae showed no detectable torsional properties. Of the tibiae of the seven killed after six weeks, three still showed no torsional properties, whilst the remaining four measured minimal torsional stiffness. The tibiae of the control group, on the other hand, were found by the torsional tests to be at a significantly more mature stage both at two and at six weeks.

The results of these tests show that load monitoring of an external fracture fixator, carried out in a manner according to the invention, gives strong evidence of delayed union as early as three weeks after fixation. In practical human medical terms, such an indication can be interpreted by a clinician as an aid in deciding whether further active intervention to encourage union should be considered. For example, the fracture site can be stimulated or bone can be grafted to the fracture site. In some cases an intramedullary nail can be introduced across the fracture to initiate union. The advantage of being able to take these measures at the earliest possible time is that it ensures the minimum possible total healing time. Moreover, the operation is surgically more straightforward than would otherwise be the case as, for example, less callus or other material might need to be excised by a surgeon. Additionally, the monitoring of fracture healing in this way permits a quantifiable comparison of different treatments.

As mentioned previously, the test used in this monitoring method is preferably a walking test, in order to encourage muscle loading of the involved bone. If the limb is being used in this way then the total force on the bone and fixator is made up of a body weight component and a component due to muscle loading. The walking test thus ensures that the bone is subjected to a force considerably higher than would otherwise be possible, thus making the test much more sensitive than previous fracture stiffness monitoring techniques, whilst maintaining the consistency and repeatability of the results. The experiments described in this specification produced results which led to the finding that, for a given subject, the muscle load on the bone is substantially directly proportional to the weight component, or measured vertical ground force. The precise role played by the muscles is not determined during the tests, but the above finding allows this role to be taken into account by way of the FSI. A treadmill is therefore not essential and other specific tests involving alternative appropriate types of loading of the limb are envisaged.

It is to be noted that, for a completely reduced fracture, axial loading will give a falsely high value of fracture stiffness index. However, as previously mentioned, a small gap can be initially left between the bone ends across the fracture, thereby providing that a valid measure of axial fracture stiffness can still be monitored by way of the test.

The method of the invention is equally suitable for application in the case of a fully reduced fracture, in which case the bending moment in the fixator frame can be used to provide the fixator load measure used in the calculation of fracture stiffness index. In the experiments described above the bending moment in the fixator was measured by means of an additional, suitably calibrated, strain gauge transducer attached to the fixator frame.

A bending FSI was calculated in a similar manner to the axial FSI, the denominator in this case being the measured fixator bending moment. The bending FSI is clearly not a dimensionless index and its actual magnitude will therefore be expected to vary from one subject to another, but appropriate calibration ensures that this fact does not affect the validity of the results. Once again the FSI values showed a noticeable increase at or about the three-week point in the case of animals of the control group, this discontinuity being absent in the case of the animals of the delayed-union group. The advantage of using a measure of bending moment in carrying out the method of the invention, apart from its applicability to well reduced fractures, is that in the case of many types of fixator the bending moment is easier to measure accurately than the axial load.

The results of successive tests carried out according to the method of the invention can be compared with prescribed results for a fracture of the type in question. For example, an indication can be provided when the results diverge from within prescribed limits, thus suggesting that the healing is not proceeding in a satisfactory manner.

Embodiments of the invention described and illustrated in this description and in the accompanying figures are given by way of example only and it is to be understood that these are not intended in any way to limit the scope of the invention.

I claim:

1. A system for use in assessing the state of union in a bone fracture in a limb, the system comprising:

a fixator including a plurality of elements for selectively engaging respective portions of the fractured bone, whereby the fixator is selectively connected across the fracture;

means operatively coupled to the fixator for providing a measure of the load carried by the fixator and for providing a signal representing the fixator load measure;

means for providing a measure of the total load passed through the limb during a specific load test and for providing a signal representing the total limb load measure; and signal processing means operatively coupled to the fixator load measure means and the total limb load measure means for processing signals representing the fixator load measure and the total limb load measure;

wherein an apparatus is provided to stimulate or encourage muscle activity in the limb during the test.

2. A system according to claim 1, including a treadmill assembly.

3. A system according to claim 1 or claim 2, wherein the fixator load measuring means is arranged to provide a measure of the fixator load in a direction substantially parallel to the long axis of the fractured bone.

4. A system according to claim 3, wherein the fixator allows movement only in said long axis direction and the fixator load measuring means comprises a strain gauge to detect such movement.

5. A system according to claim 4, wherein the fixator comprises two separate blocks, a spring unit incorporating the strain gauge being mounted between said blocks.

6. A system according to claim 1, wherein the total limb load measuring means comprises a forceplate.

7. A system according to claim 2, wherein the total limb load measuring means comprises a forceplate and wherein the forceplate forms part of the treadmill assembly.

8. A system according to claim 1, including means to measure the bending moment in the fixator.

9. A method for use in assessing the state of union in a bone fracture in a limb of a subject, for which fracture a fixator has been applied, the method comprising the steps of:

providing a fixator including a plurality of elements for selectively engaging respective portions of the fractured bone;

connecting the fixator across the fracture;

operatively coupling means for providing a measure of the load carried by the fixator to the fixator;

providing means for providing a measure of the total load passed through the limb during a specific load test;

operatively coupling signal processing means to the fixator load measure means and the total limb load measure means for processing signals representing the fixator load measure and the total limb load measure;

providing an apparatus to stimulate or encourage muscle activity in the limb during the test;

subjecting the limb to a specific load test involving the application of muscle loading to the limb;

measuring the load carried by the fixator and the total load passed through the limb during the test; and determining a measure representing a comparison between the measured fixator load and the total limb load.

10. A method according to claim 9, wherein the test is a walking test.

11. A method according to claim 10, wherein the test is carried out on a treadmill and the total limb load is determined by measuring the vertical ground force exerted by the limb on the treadmill.

12. A method according to claim 10 or claim 11, wherein only a selected part of each step of the walking test is considered for purposes of determining the load comparison measure.

13. A method according to claim 12, wherein the selected part is a central portion of the stance phase of each step.

14. A method according to claim 9, wherein the test is carried out at successive intervals after fixation and the results of successive tests are compared with prescribed results for a fracture of the type in question.

15. A method according to claim 9, wherein the measure of comparison is a fracture stiffness index (FSI), or its reciprocal, wherein FSI is defined as:

FSI=Total limb load/Fixator load.

* * * * *